United States Patent
Lerum et al.

(10) Patent No.: US 12,337,059 B2
(45) Date of Patent: Jun. 24, 2025

(54) BIOBASED, BIODEGRADABLE COMPOSITE POWDER FOR USE IN COSMETICS

(71) Applicant: Grant Industries, Inc., Elmwood Park, NJ (US)

(72) Inventors: Ronald V. Lerum, Leonia, NJ (US); Anna K. Croom, Brooklyn, NY (US); Tania Viana, Ridgewood, NJ (US); Aga Pawlik, Hasbrouck Heights, NJ (US)

(73) Assignee: GRANT INDUSTRIES, INC., Elmwood Park, NJ (US)

( * ) Notice: Subject to any disclaimer, the term of this patent is extended or adjusted under 35 U.S.C. 154(b) by 142 days.

(21) Appl. No.: 17/479,122

(22) Filed: Sep. 20, 2021

(65) Prior Publication Data
US 2022/0087928 A1    Mar. 24, 2022

Related U.S. Application Data

(60) Provisional application No. 63/080,820, filed on Sep. 21, 2020.

(51) Int. Cl.
*A61K 8/44* (2006.01)
*A61K 8/02* (2006.01)
(Continued)

(52) U.S. Cl.
CPC .............. *A61K 8/99* (2013.01); *A61K 8/0241* (2013.01); *A61K 8/44* (2013.01); *A61K 8/732* (2013.01);
(Continued)

(58) Field of Classification Search
CPC .......... A61K 8/99; A61K 8/0241; A61K 8/44; A61K 8/732; A61K 2800/412; A61Q 1/12; A61Q 17/04
See application file for complete search history.

(56) References Cited

U.S. PATENT DOCUMENTS 4,485,092 A    11/1984 Ashton et al.
4,568,539 A    2/1986 Ashton et al.
(Continued)

FOREIGN PATENT DOCUMENTS

CN    102056985 A    5/2011
EP    3560479 A1    10/2019
(Continued)

OTHER PUBLICATIONS

Anders G. Sandstrom, et al., "Engineering of *Saccharomyces cerevisiae* for the Production of Poly-3-D-Hydroxybutyrate From Xylose", AMB Express, vol. 5, No. 14, pp. 1-9, 2015.
(Continued)

*Primary Examiner* — Bethany P Barham
*Assistant Examiner* — Ayaan A Alam
(74) *Attorney, Agent, or Firm* — LUCAS & MERCANTI, LLP (57) ABSTRACT

Cosmetic compositions useful intended for use in cosmetics and personal care formulations are disclosed. The cosmetic compositions include a micronized, substantially uniform powder mixture of a ferment containing a polyhydroxyalkanoate such as polyhydroxybutyrate and an amino acid derivative such as the lysine derivative N6-lauroyl-L-lysine. The cosmetic powder compositions can be intermediates that enhance the textural profile of cosmetics providing sensorial improvement, and/or soft-focus effects, line blurring effects by filling unevenness in the skin, making it appear smoother with less skin imperfections and wrinkles. The powder-based compositions can serve as detackifiers and/or viscosity modifiers due to its ability to absorb oil. The powder provides formulation options for cosmetics and personal care formulas prepared from biobased and biodegradable materials. Methods of preparing the powder com-
(Continued)

Relationship between wt.% of the powder composite 11A-D and the % relative shine.

positions, as well as cosmetics containing the composition are also disclosed.

26 Claims, 1 Drawing Sheet

(51) Int. Cl.
*A61K 8/73* (2006.01)
*A61K 8/99* (2017.01)
*A61Q 1/12* (2006.01)
*A61Q 17/04* (2006.01)

(52) U.S. Cl.
CPC ............... *A61Q 1/12* (2013.01); *A61Q 17/04* (2013.01); *A61K 2800/412* (2013.01)

(56) References Cited

U.S. PATENT DOCUMENTS

| | | | |
|---|---|---|---|
| 5,683,706 | A | 11/1997 | Lafleur et al. |
| 6,080,424 | A | 6/2000 | Avalle |
| 6,296,860 | B1 | 10/2001 | Hasegawa et al. |
| 6,703,517 | B2 | 3/2004 | Hattori et al. |
| 6,709,848 | B1 | 3/2004 | Martin et al. |
| 7,160,550 | B2 | 1/2007 | Brieva et al. |
| 8,968,787 | B2 | 3/2015 | Gittleman |
| 9,683,076 | B2 | 6/2017 | Begotti |
| 9,688,603 | B2 | 6/2017 | Smith et al. |
| 2005/0074473 | A1 | 4/2005 | Kosbach et al. |
| 2006/0233728 | A1 | 10/2006 | Sagawa et al. |
| 2009/0263660 | A1 | 10/2009 | Takeuchi et al. |
| 2011/0048284 | A1 | 3/2011 | Choi et al. |
| 2020/0268637 | A1 | 8/2020 | Czarnecki |

FOREIGN PATENT DOCUMENTS

| | | |
|---|---|---|
| IT | 201900003981 A1 | 9/2020 |
| JP | 2000053534 A | 2/2000 |
| JP | 2005154649 A | 6/2005 |
| WO | 2011016140 A1 | 2/2011 |
| WO | WO-2017104587 A2 * | 6/2017 |
| WO | 2018178899 A1 | 10/2018 |
| WO | 2020188439 A1 | 9/2020 |

OTHER PUBLICATIONS

Slaninova, "Light Scattering on PHA Granules Protects Bacterial Cells Against the Harmful Effects of UV Radiation", 1923-1931, Appl Microbiol Biotechnol., Abstract (1 page), 2018.
Uta Breuer, et al., "Yeasts as Producers of Polyhydroxyalkanoates: Genetic Engineering of *Saccharomyces cerevisiae*", Macromolecular Bioscience, vol. 2, No. 8, Abstract (3 page), 2002.
International Search Report and Written Opinion for International Application No. PCT/US2021/051044 (9 Pages) (Feb. 18, 2022).
Anonymous: "Granpowder BBP-700 100% Naturally Derived, Bio-Based Powder", pp. 1-2, Jul. 14, 2021, XP093041148.
Fillardet Laurence, "Spherical Powder of PHA for Cosmetic Applications", Research Disclosure, vol. 667, No. 62, pp. 1-14, 2019.
Extended European Search Report for Corresponding European Application No. 21870360.1, Oct. 10, 2024, 12 Pages.

* cited by examiner

Relationship between wt.% of the powder composite 11A-D and the % relative shine.

BIOBASED, BIODEGRADABLE COMPOSITE POWDER FOR USE IN COSMETICS

CROSS-REFERENCE TO RELATED APPLICATIONS

This application claims the benefit of priority from U.S. Provisional Patent Application Ser. No. 63/080,820, filed Sep. 21, 2020, the contents of which are incorporated herein by reference.

FIELD OF THE INVENTION

The present invention is directed to powder compositions useful in cosmetic compositions intended for use on the body, face, hair, and around the eyes.

BACKGROUND OF THE INVENTION

Powders introduced into cosmetic formulations enhance the textural profile, provide soft-focus effects, and improve the ease of incorporation into a formulation. Powders are known in cosmetics and personal care formulations to provide oil absorbance/mattifying, modify rheology parameters, provide film-forming applications, SPF boosting in sunscreen applications and to enhance the overall aesthetic skin-feel or glide of a product during application. Typically, powders used in cosmetics are synthetic in origin or obtained from minerals. Powders that are synthetic in origin are derived from fossil fuel feedstocks and are necessarily bio-persistent. Bio-persistent powders may degrade but are not biodegradable. Powders derived from bio-based often possess the characteristic of being biodegradable and sustainably sourced but fail to achieve parity in texture and formulation performance compared to their fossil fuel derived counterpoints. Toward the goal of developing cosmetic and personal care products from sustainable sources, and to avoid persistence in the environment as waste, it is advantageous to develop a powder for cosmetic and personal care use that provides excellent sensorial properties and ease of formulation.

SUMMARY OF THE INVENTION

In one aspect of the invention, there are provided powder compositions useful in the manufacture of cosmetic formulations or cosmetic compositions. The powder compositions include a micronized mixture of a ferment obtained from a micro-organism, bacteria or yeast such as a polyhydroxyalkanoate in an amount from about 50% to 99.9% by weight of the composition; and an amino acid derivative such as an N-acylated amino acid, for example, an N-acylated lysine in an amount from about 0.1% to 50% by weight of the composition.

The ferment and the amino acid derivative are mixed and micronized under conditions to provide the powder composition with coefficient of friction of from about 0.1 to about 0.25. The physical properties of the resultant powder composition are different from powder compositions formed by merely mixing the two components or by micronizing the components of the powder at room temperature.

In some embodiments, the ferment is present in an amount of from about 80% to about 95% by weight and the amino acid derivative is present in an amount of from about 5 to about 20%.

The ferment and the amino acid derivative are each in particulate form and are in a substantially uniform mixture with each other, preferably achieved by mixing and micronizing the two components simultaneously or substantially simultaneously into a fine powder blend under conditions which include mixing and micronizing the ingredients until the temperature of the powders reach a temperature of about 105° C. or greater, and in some aspects within a range of from about 107° C. to about 165° C. and thereafter holding the micronized blend, preferably under mixing conditions for a sufficient time to achieve the desired properties. For example, hold times of at least about 15 minutes have been determined to be sufficient while in other aspects time periods of about an hour are used and in some further embodiments, the amount of time is from about 1 to about 3 hours before being allowed to cool. The resultant powder compositions also preferably demonstrate no water absorption properties and are generally regarded as hydrophobic.

The powder compositions may also include ancillary cosmetically acceptable ingredients, if desired, which may be blended with the two components either as part of the micronization or as part of a separate blending after the micronization of the two components.

The invention also includes processes of preparing the powder compositions having the desirable coefficient of friction and/or hydrophobicity by micronizing the blend of ferment and amino acid under conditions described herein.

The powder mixture can be included in various cosmetics in amounts of from about <1% by weight to amounts of about 99% by weight, depending upon the type of cosmetic. In some aspects the amount included is at least about 1% by weight to about 50% by weight of topical cosmetics or topical pharmaceutical formulations and in other embodiments such as body powders, the amount of the inventive powder composition can be from about 50 to about 99% by weight.

The powder compositions of the invention are useful in imparting or enhancing a soft-focus effect in various cosmetics. This can be achieved by including at least about 1% wt. of the powder compositions described herein. Alternatively, the soft-focus cosmetic compositions can include from about 1 to about 30% wt of the powder compositions described herein. As such a method of enhancing the soft-focus effect of a cosmetic composition is provided by combining the cosmetic composition with at least about 1% wt. of the inventive powder compositions described herein.

In other aspects, the inventive compositions impart an ability to the cosmetic to aid in hiding or disguising skin imperfections by being present in the cosmetic products in the amounts described herein. Therefore, the invention further includes methods of disguising skin imperfections on a mammal skin surface by applying a cosmetic composition containing a sufficient amount of the powder compositions described herein, e.g. at least about 1% by weight of the cosmetic composition to the area of the skin requiring the cosmetic treatment.

In a further aspect of the invention, the powder compositions described herein are useful stabilizing cosmetic formulations by being included in the cosmetic formulations in the amounts described herein. The powder compositions impart oil suspending and sorbing capabilities to the cosmetic formulation thereby increasing viscosity of the final cosmetic composition. In such embodiments, the inventive powder compositions are included in amounts of at least about 1% wt.

Still further aspects of the invention include methods of preparing the powder compositions and cosmetic products including the powder compositions.

DETAILED DESCRIPTION OF THE INVENTION

The cosmetic compositions used in this invention, i.e. which include the micronized powder blend of ferment and amino acid derivative, include but are not limited to lotions, creams, serums, mousse, sunscreens, BB creams, foundations, concealers, liquid or stick highlighters, moisturizers, liquid or stick contouring, lip color, such as lipsticks and liquid lipsticks, lip glosses, lip care, such as lip moisturizers and lip balms, all in the form of emulsions or anhydrous face and body loose powders, face pressed powders, and for periorbital skincare formulations such as eye-creams and serums, and mascaras, eyeliners, eyeshadows, and eyebrow applications. Additional applications of the novel powder compositions include but are not limited to shampoos, leave-on and rinse-off conditioners, rinse-off and leave-on hair masks, hair serums, dry shampoos and hair texturizing formulations in the form of loose powder or aerosols. The invention displays the benefit of providing a powder with ease of formulation, enhanced formulation stability, as well as textural and physical appearance enhancements and SPF boosting properties. The cosmetic powders can have the functions to enhance skin conditioning, reduce shine, mattifying properties to reduce fine lines by filling in tiny gaps on the skin due to ageing; have sorbent properties; enhance sensorial attributes, such as softening, lubricity and smoothing, and can contribute to even coverage of makeup applied to skin as well as strengthening the color and pigment properties in various cosmetics.

Particle size and agglomerate nature are correlated to the textural profile of cosmetic compositions, including the perception of glide across the skin, the persistence of tack and film forming properties, as well as optical attributes such as line-filling, soft-focus, line blurring effects. A uniform, narrow particle size contributes to an even distribution of cosmetic applications onto the skin with higher surface area spreadability, which contributes to a boost in SPF. As such, a further aspect of the invention includes methods for achieving SPF boost in sunscreen applications of a cosmetic. The methods include combining the cosmetic composition ingredients with at least 1 wt. % of the micronized powder composition described herein.

The powders in this invention can, in some embodiments, have a particle size range of from about 0.1 to about 120 microns. In further embodiments, the powder compositions have a particle size of from about 0.1 to about 50 microns. The powders can have shapes that are spherical; irregular; or fibrous-like. Powders can be discrete particles, aggregated, clusters or agglomerates.

The powder compositions in this invention can be obtained by use of mechanical agitation, such as, tumblers, mixers, V-blenders, etc. to first create a physical blend of the ferment and amino acid derivative before being placed into a reaction vessel Alternatively, the ferment and amino acid derivative can be directly added to a reaction vessel where they are blended and micronized. The powder compositions of this invention are prepared by the use of size reduction or micronizing machines, such as, jet mill, hammermill, knife mills, planetary mills, roller mills, blender, etc. to achieve the desired particle size distribution.

For example, the ferment and the amino acid derivative, either as a binary mixture or optionally in combination with other ingredients, can be initially combined and, optionally intimately mixed using blending as mentioned above, prior to micronization. Thus, the mixture of components which comprise the powder compositions after micronization under the conditions described herein, i.e. the ferment and amino acid derivative, are preferably an intimate mixture wherein the ferment particles and amino acid derivative particles are thoroughly intermingled with one another, forming a substantially uniform mixture and, after micronization under the conditions described herein, yield powder compositions with a coefficient of friction of 0.1 to 0.25 and, preferably, are hydrophobic and/or have zero water absorption. Those of ordinary skill will appreciate that the powder compositions in this invention may require the use of sieve mesh to remove large grainy particulates. In some aspects of the invention, the inventive powder compositions are free-flowing powders and can have a bulk density of from about 0.15 g/mL to about 0.25 g/mL. In other aspects, the bulk density ranges from about 0.19 to about 0.24 g/ml.

The conditions under which the blend of the ferment and amino acid derivative are micronized to yield the final powder composition with the desired coefficient of friction include a combination of time and temperature under which the blend is undergoing a micronizing process. Generally speaking, the mixing and micronizing of the ferment and amino acid derivative is continued until the mixture reaches a temperature of the powder reaches a temperature of at least about 105° C. or greater, and in some aspects within a range of from about 107° C. to about 165° C. Once the desired temperature is reached, the powder blend is held for at least about 15 minutes and, in some embodiments, for about 1 hour or in some aspects, for a time period of from about 1 hour to about 3 hours at the temperatures mentioned. The powder compositions are then allowed to cool before being sieved. It will be understood that the temperatures and times mentioned will vary somewhat depending upon the volume of powder blend to be processed, apparatus used for micronization and other factors known to those of ordinary skill. It will further be understood that during the period in which the powder blend is being held at the desired temperature that the powders will continue to be blended or otherwise agitated so that the temperature can be maintained within the desired range. Preparing the powder compositions having the desired properties, however, is achievable without undue experimentation. An example of the type of process used make use of a professional high variable manual speed blender. This can be thought of as mixing and micronization that requires significant amounts of energy and heat by means of friction. Examples of professional blenders were the Oster Versa Pro Series Blender and Waring Commercial Blender Model MX1200. The blenders were equipped with a stainless steel 64 oz jar and a digital thermometer with a Type-K thermocouple. The power and temperature of the blender was controlled manually with variable speed controls from 1,500 to 20,000 RPM.

Size reduction is known to those skilled in the art and will determine the proper conditions to obtain particles with the desired size for enhanced texture. The enhanced texture will provide cosmetic formulations with a soft powdery and smooth feel, better lubricity, slip and improved spreadability as well as soft-focus or line-blurring effects. It is known to those skilled in the art that particle sizes greater than 80 microns feel grainy and provide no soft-focus. Therefore, powder compositions with larger particle size particles can be used in scrub and exfoliation cosmetic compositions.

Also known to those skilled in the art that particle size and shape are not the only factor for better texture and soft-focus. Other attributes this invention seeks to solve is to provide better spreadability for natural even coverage and a silky feel, to provide enhanced skin substantivity, improving long wear and transfer-resistance with reduction of tack and sticky feel. By reducing tack, the cosmetic product will have better long wear coverage and there will be no need for reapplication of the product on skin. Therefore, minimizing the potential of skin defects.

The powder compositions of the invention have the benefit of being biodegradable powders, whereby microorganisms are able to enzymatically metabolize the product through either an anaerobic or aerobic biochemical process. Biodegradable materials are metabolized into water, carbon dioxide, and biomass with the help of microorganisms. This powder serves as a food source composed of enzymatically cleavable linkages such as esters and amides.

Cosmetic compositions containing powders may originate from minerals. Examples of mineral-based powders include, mica, kaolin, aluminosilicate, boron nitride, silicone dioxide, talc, apatite and the like.

Cosmetic compositions containing powders may be synthetic in origin. Synthetic powders are defined as fossil fuel derived and examples include but are not limited to polyamide (nylon), polyethylene, poly (methyl methacrylate), polypropylene, polytetrafluoroethylene and ethylene/acrylate cross-polymers. The powder compositions described herein can be used to replace a portion or all of the powders of synthetic origin in most cosmetic formulations.

Cosmetic compositions containing powder may be natural from origin. Natural powders are defined as obtained from plants or microorganisms, such as cellulose, starch, glycoprotein, such as silk protein powder, polylactic acid, polyesters, such as, polybutylene succinate and polyhydroxyalkanoates and derivatives of polyhydroxyalkanoates. The inventive powder compositions can likewise be used in these types of cosmetics to replace a portion or all of the powder components therein.

The powder compositions of the invention comprise, consist essentially of, or consist of a micronized mixture of a ferment and an amino acid derivative. The ferment can be in an amount of about 50% to 99.9% by weight of the powder composition and the amino acid derivative can be present in an amount of about 0.1% to 50% by weight of the composition. In alternative aspects of the invention the amount of ferment is from about 80% to about 95% and the amount of amino acid derivative is from about 5% to about 20% by weight 5%, respectively.

The powder compositions may include one or more ancillary ingredients which are cosmetically acceptable, such as but not limited to, ingredients favorably included in a desired cosmetic composition. For example, preservatives, fragrances or odor neutralizers may be incorporated by either co-micronization with the primary components or as part of a subsequent blend with the micronized ferment and amino acid derivative mixture. An ingredient may also be introduced into the inventive powder compositions to obtain a different functionality from that observed from compositions omitting the ancillary ingredient. A non-limiting list of exemplary ancillary ingredients which can be added include solid/semi-solid oils such as, silicone oil, petrolatum, lanoline, beeswax, candelilla wax, squalane, emollients, ester oils, water-soluble polymers, carbowax, polyethylene glycols, a coloring dye, inorganic and organic pigments, preservative cocktails, glycerol, phenethyl alcohol, caprylyl glycol, benzoic acid, phenoxyethanol, potassium sorbate, pH adjusters, citric acid, sodium hydroxide, antioxidants, fragrance, odor neutralizers, cyclodextrins, ultraviolet absorbers, inorganic and organic sunscreens, zinc oxides, titanium oxides, avobenzone, skin activating agents, retinol, hydroxypinacolone retinoate, retinaldehyde, etc., the only limitation being that the ancillary ingredient does not spoil or degrade the powder composition or any cosmetic composition it was included in.

For purposes of the present invention, "ferment" shall be understood to mean an ingredient obtained from microorganisms by a fermentation process and known to those of ordinary skill in the art. Fermentation is a metabolic process that produces chemical changes in organic substrates through the action of enzymes. The fermentation process occurs by the controlled use of microorganisms. Fermentation in the absence of oxygen allows for the conversion of sugars, such as, glucose, lactose, whey or propionic acids to be converted to polyesters. The process of fermentation by this invention leads to a class of renewable, biodegradable, and bio-based polymers in the form of polyesters. One such polyester product obtained is called polyhydroxyalkanoate (PHA), more specifically derivatives of polyhydroxybutyrate. The biomass recovery of this fermented solid polyester extract, requires sterilization, lysing of the microorganism, isolating the PHA from the microorganism fragments, concentrating by centrifuge or filter press and rinsing to obtain purified granular PHA and then dried. The dried fermented solid obtained is preferably a PHA derivative and used in this invention. The ferment obtained in this invention is solid and can have a melt point of 150° C. to 180° C. In other aspects of the invention, the ferment or products which are a result of a fermentation and extraction process are available from commercial sources such as BioMateria; Bio-on; Danimer Scientific; TianAn Biologic; Tianjin GreenBio; Metabolix; Mango Materials and others.

One such microorganism useful in providing the ferment is a type of yeast belonging to the genus *Saccharomyces*. Microorganisms such as *Saccharomyces cerevisiae*, also known as "Baker's yeast," have been used for 10,000 years in the production of wine, beer, bread, vinegars and other commodities. More recently, this fermentation process is being employed for the production of bio-based raw materials that are also inherently biodegradable.

In some embodiments, the PHA is polyhydroxybutyrate (PHB), polyhydroxyvalerate (PHV), polyhydroxybutyratevalerate (PHBV), or polyhydroxyhexanoate (PHH), or a derivative of the foregoing and/or a combination thereof. Known to those skilled in the art, other microorganisms involved in the fermentation of polyhydroxyalkanoates and derivatives include but are not limited to bacterial in origin, such as, *Cupriavidus necator, Alcaligenes latus, Alcaligenes eutrophus, Escherichia coli, Pseudomonas putida*, and *Aeromona hydrophila*. Genetically-engineered organisms known in the art may also be used for fermentation of a feedstock to produce PHAs. In further embodiments, suitable ferments or PHA's are those which comprise at least one of the following polymeric and/or copolymeric structures: poly-3-hydroxybutyrate (P-3HB), poly-3-hydroxy-butyrate-co-3-hydroxyvalerate (P-3HB-3HV), poly-3-hydroxybutyrate-co-4-hydroxybutyrate (P-3HB-4HB), and poly-3-hydroxybutyrate-co-3-hydroxyvalerate-co-4-hydroxybutyrate (P-3HB-3HV-4HB). See also US Patent Application Publication US2020/0268637A1, the disclosure of which is incorporated herein by reference.

The second component of the powder composition in this invention is the amino acid derivative. Some preferred amino acid derivatives are N-Acylated amino acids, such as N-acylated lysine derivatives, wherein the acyl group represents an amide bond and an alkyl of 2 to 15 carbon atoms, more specifically N6-lauroyl-L-lysine and N6-capryloyl-L-lysine. N-Acylated amino acids are known to be biodegradable. N-acylated amino acids can be natural or synthetic in origin. A non-limiting list of commercially available N-acylated amino acids include N6-lauroyl-L-lysine (lauroyl lysine) and, N6-capryloyl-L-lysine, N-undecylenoyl amino acids such as undecylenoyl phenylalanine and undecylenoyl glycine, N-palmitoyl-amino acids such as palmitoyl arginine, palmitoyl glycine, palmitoyl proline, palmitoyl serine, and palmitoyl lysyl aminovaleroyl lysine, N-cocoyl amino acids such as N-cocoyl glutamic acid, N-capryloyl amino acids such as capryloyl glycine and capryloyl serine, N-acetyl amino acids such as acetyl cysteine, acetyl glutamic acid, acetyl glutamine, and diethyl acetyl aspartate, as well as oleoyl tyrosine, lauroyl aspartate, and stearoyl glutamic acid.

Treatment of fine powders with N-acylated lysine and derivatives thereof improve sensorial and tactile feeling as well as improving spread-ability of the cosmetic composition. Another benefit from the treatment of these fine powders with N6-lauroyl-L-lysine is its hydrophobicity, which cannot be achieved by sole use of PHA. Having the fused powder composite helps avoid the migration of the powder to the water phase of the cosmetic formulation. The fused composite has a better suspension throughout the cosmetic formula making it more homogenous. This hydrophobicity and homogeneity of the formula enhances formulation compatibility resulting in a better stability and longer shelf life.

An important feature of the present invention is the ability of the composition treatment with N-acylated lysine and derivatives to enhance the flow behavior of the untreated powder. The addition of N-acylated lysine and derivates in the ranges described herein, particularly when in the range of 5 to 20% by weight to the ferment/polyhydroxyalkonate via co-micronization promoted flow during manufacturing and processing, or eliminated caking, stickiness and agglomeration. In contrast, the isolated ferment powder or polyhydroxyalkanoate powder alone does not flow well and self-agglomerates, therefore increasing the difficulty of incorporation into cosmetic formulations. The inventive compositions are preferably free-flowing powders.

This invention answers the demand for powders that are both easy and beneficial to formulate. This powder mixture or composite is easy to incorporate into formulations without creaming or sedimentation, flocculation, coalescence or separation, sweating or undesirable viscosity changes. These behaviors are commonly observed as a formula becomes unstable. The powder compositions were found to possess the versatility to be incorporated into any specific cosmetic formulation via hot or cold processes, without particle deformation, melting, or phase separation. A particularly advantageous aspect of this invention is the ability to post-add into a cosmetic formulation without the need to pre-disperse. For example, certain powders clump easily upon addition to formulation, therefore extra steps were required to assist the incorporation of the powder.

In addition, the powder composite in this invention exhibits good affinity to the skin and contributes to a favorable texture during application in a finished cosmetic formulation. The powder composite displays enhanced lubricity with better slip and glide. The absorbance properties allow skin oil to be absorbed proving a smoother application and tack reduction in a cosmetic or personal care composition wherein the powder mixture or composite described herein can be included in amounts of from about 1 to about 50% by weight. It is further contemplated that the inventive powder composites can be included in amounts below or above the aforementioned ranges in cosmetic compositions if desired by the artisan without undue experimentation.

The powder composite in this invention performs desirable optical properties such as reduction of gloss and enhancing mattifying properties upon application of a finished cosmetic formulation. This behavior known to the art is called soft-focus. The resulting cosmetic products can minimize the flaws of skin wrinkles due to ageing, therefore obtaining a younger skin appearance due at least in part to the presence of the inventive mixtures being present in the cosmetic formulation.

The present invention also relates to body powder compositions. Body powders are used in the cosmetic industry and marketed for absorbing moisture, odor control, cooling sensation, and relief from skin irritation or rash. Due to the potential link between ovarian cancer and talcum powder, a search for talc-free body powder with the same performance is ongoing. It is the object of this invention to provide a replacement for talcum powder for applications in body powder compositions. In addition, talcum powder acts as a filler and an absorbent in the formulation. Applications containing talcum powder causes the product to lose its silky luxurious feel. Among other components that are traditionally found in body powder compositions are perfumes, dyes, medicaments, and antimicrobial agents. Examples of body powders in accordance with this aspect of the invention include which contain from about 50 to about 99% by weight of the powder compositions described herein containing the micronized ferment and amino acid derivative. The remainder can include from about 1 to about 50% by weight cornstarch or a mixture of cornstarch and other cosmetically acceptable ancillary ingredients. Alternatively, some suitable body powder compositions can include from about 70 to about 99% by weight of the inventive powder composition and from about 1 to about 30% by weight cornstarch or cornstarch mixtures.

Examples for perfume components include one or more components but not limited to three major groups known to the art. The top notes, which tend to dissipate rapidly upon application; the middle notes, which dissipate over a few hours after application, and the base notes, which dissipate slowly over the course of the day after application. Examples of top notes include lemon, grapefruit, lavender; examples of middle notes, include geranium, chamomile, cinnamon; and examples of base notes, include tea tree, eucalyptus, vanilla. In these aspects of the invention, the amount of inventive mixture included in the perfume or cologne can be from about 0.01 to about 1.0% by weight of the total composition.

Gloss Meter

An instrument used to measure gloss is a glossmeter. A gloss meter is a tool used to measure the amount of reflected light and is done by projecting a beam of light at the surface and measuring the intensity of the beam at the equal and opposite angle. This measurement is recorded in Gloss Units (GU) where a higher value indicates a more reflective, shiny surface and a lower value indicates a more matte surface. While there are different angles GU can be measured, 60° was the universal angle used. The procedure to measure gloss was done by using a 5 mil drawdown bar to apply a cosmetic formula on a sheet of Leneta paper. The formula was applied and in a swift and steady motion as the drawdown bar was pulled downward toward the end of the paper. The film was allowed to air-dry for 2-24 hours and then measured using a glossmeter. The measurement was performed in triplicate.

Coefficient of Friction

The coefficient of friction is a value that indicates the amount of resistance a substance experiences between two substrates. There are two types of Coefficient of friction: static and kinetic. Static friction is the force required to start moving an object and kinetic friction is the force required to maintain that movement. Kinetic coefficient of friction can also be seen as a sliding or lubricity force where a lower value indicates an object's ease of glide. ASTM-D1894 "Standard Test Method for Static and Kinetic Coefficients of Friction of Plastic Film and Sheeting" was modified to measure a powder's coefficient of friction due to the lack of a proper ASTM method for powders. All testing parameters followed were consistent in sample thickness, testing speed and distance, and value calculations. A Texture Analyzer TA.XT Plus fitted with a coefficient of friction sled was used to measure friction. Briefly, a 4% by weight of powder in isopropanol was prepared and applied to a Leneta paper by a 5 mil drawdown bar, pulled downward in a swift, steady motion. The film was allowed to air dry overnight and the coefficient of friction was evaluated. In many aspects of the invention, the powder compositions have a coefficient of friction of from about 0.1 to about 0.8, and preferably a coefficient of friction of about 0.1 to about 0.3.

Liquid Absorption of Powders by Spatula Rub-Out

ASTM-D281 is a method that covers the determination of the liquid absorption of powders by the spatula rub-out technique. The value obtained by this method gives information about the vehicle demand of the powder when it is used in a powder paste. Liquid absorption values can be used to characterize powders or batches of a given powder.

Weigh exactly 0.5 g, or any multiple thereof, air dried powder was placed upon a glass plate or marble slab. Weigh to 0.01 g a dropping bottle containing liquid along with the pipet and rubber bulb. Add the liquid gradually, drop by drop (by means of the pipet), to the powder. After the addition of each drop, thoroughly incorporate the oil by rubbing up with the spatula. The test was complete when exactly enough oil has been incorporated with the pigment to produce a very stiff, putty-like paste "ball", that does not break or separate or smear. Weigh the bottle and liquid to 0.01 g and determine by difference the weight of oil used. From the weights of the liquid and powder used in the test, calculate the number of grams of liquid to exactly wet grams of liquid per 100 grams of powder.

EXAMPLES

General Procedure

Examples 1 through 5 and Example 7 were followed according to this General Procedure. The PHA Ferment and N6-lauroyl lysine were added to a reactor vessel, such as a Waring Commercial Blender Model MX1200. The blenders were equipped with a stainless steel 64 oz jar and a digital thermometer with a Type-K thermocouple. The power and temperature of the blender was controlled manually with variable speed controls. The mixture was mixed and micronized until the mixture reached 105° C.-165° C. Once temperature was achieved there was a necessary hold time of 15 minutes to 3 hours to yield the desired product. The powder was allowed to cool to 50 C, sieved through a stainless steel No. 200 Mesh (75 micron) and then collected into a container. The particle size was therefore nominally below 80 microns. The particle size distribution analysis was determined to have a range of 1 to 10 microns (by number).

Example 1

95 parts of the PHA Ferment and 5 parts N6-lauroyl lysine were added to the Waring Commercial Blender Model MX1200. By use of the variable speed controller. The temperature of the reactor was allowed to reach 150 C and held for 45 minutes. The powder was allowed to cool to 50° C., sieved through a stainless steel No. 200 Mesh and collected into a container. The coefficient of friction was determined to be 0.232 and the powder was hydrophobic.

Example 2

90 parts of the PHA Ferment and 10 parts N6-lauroyl lysine were added to the Waring Commercial Blender Model MX1200. By use of the variable speed controller, the temperature of the reactor was allowed to reach 150° C. and held for 60 minutes. The powder was allowed to cool to 50° C., sieved through a stainless steel No. 200 Mesh and collected into a container. The coefficient of friction was determined to be 0.229 and the powder was hydrophobic.

Example 3

90 parts of the PHA Ferment and 10 parts N6-lauroyl lysine were added to the Waring Commercial Blender Model MX1200. By use of the variable speed controller, the temperature of the reactor was allowed to reach 107° C. and held for 3 hours. The powder was allowed to cool to 50° C., sieved through a stainless steel No. 200 Mesh and collected into a container. The Coefficient of friction was determined to be 0.226 and the powder was hydrophobic.

Example 4

85 parts of the PHA Ferment and 15 parts N6-lauroyl lysine were added to the Waring Commercial Blender Model MX1200. By use of the variable speed controller, the temperature of the reactor was allowed to reach 150° C. and held for 15 minutes. The powder was allowed to cool to 50° C., sieved through a stainless steel No. 200 Mesh and collected into a container. The Coefficient of friction was determined to be 0.231 and the powder was hydrophobic.

Example 5

80 parts of the PHA Ferment and 20 parts N6-lauroyl lysine were added to the Waring Commercial Blender Model MX1200. By use of the variable speed controller, the temperature of the reactor was allowed to reach 150° C. and held for 15 minutes. The powder was allowed to cool to 50° C., sieved through a stainless steel No. 200 Mesh and collected into a container. The Coefficient of friction was determined to be 0.221 and the powder was hydrophobic.

Example 6

70 parts of the PHA Ferment and 30 parts N6-lauroyl lysine were added to the Waring Commercial Blender Model MX1200. By use of the variable speed controller, the temperature of the reactor was allowed to reach 150° C. and held for 60 minutes. The powder was allowed to cool to 50° C., sieved through a stainless steel No. 200 Mesh and collected into a container. The Coefficient of friction was determined to be 0.193 and the powder was hydrophobic.

Example 7 (Comparative)

90 parts of the *Saccharomyces* Ferment and 10 parts N6-lauroyl lysine were added to the Waring Commercial Blender Model MX1200 for 60 minutes. The mixture was micronized and mixed below 60° C. until a homogeneous mixture was obtained. The power and temperature of the blender was controlled manually with a variable speed controller. The powder was sieved through a stainless steel No. 200 Mesh (75 micron) and then collected into a container. The particle size was therefore nominally below 80 microns. The Coefficient of Friction was 0.268 and the powder was not hydrophobic. This powder was not found to be free flowing, was found difficult to formulate in a cosmetic product and had poor formulation stability.

Example 8 (Comparative)

100 parts of the *Saccharomyces* Ferment was added to the Waring Commercial Blender Model MX1200. The temperature of the reactor was allowed to reach 140 C and held for 15 minutes. The powder was allowed to cool 50° C. but was not able to be sieved. The powder was not free-flowing and had melted together under this General Procedure.

TABLE 1

| | Examples | | | | | | | |
|---|---|---|---|---|---|---|---|---|
| | 1 | 2 | 3 | 4 | 5 | 6 | 7 | 8 |
| PHA Ferment | 95 | 90 | 90 | 85 | 80 | 70 | 90 | 100 |
| N6-lauroyl lysine | 5 | 10 | 10 | 15 | 20 | 30 | 10 | 0 |

Evaluation of Powder

The powders were passed through a 200 mesh (75 micron) to remove large undesired particulates. In this experiment, a hydrophobic powder was defined as a powder that does not disperse in water. Whereby, a positive sign (+) was hydrophobic and a negative sign (−) does not disperse in water. The relative hydrophobicity of the powders can be qualitatively determined. This was performed by taking 1 gram of powder and adding 10 grams of water to a 4 oz jar. The contents were stirred with a spatula. Powder that did not disperse in the water and remained afloat were labelled hydrophobic. This hydrophobicity was a desirable attribute of the final powder.

Smoothness was defined as easily gliding when applied to skin. Whereby, a scale of 1-3 was given. A scale of 1 was given for poor smoothness and a scale of 3 was given excellent smoothness. Smoothness was evaluated by personnel trained in haptic perception.

TABLE 2

Powder evaluation

| Samples | Hydrophobic | Smoothness | Coefficient of Friction |
|---|---|---|---|
| Example 1 | + | 2 | 0.232 |
| Example 2 | + | 3 | 0.229 |
| Example 3 | + | 3 | 0.226 |
| Example 4 | + | 3 | 0.231 |

TABLE 2-continued

Powder evaluation

| Samples | Hydrophobic | Smoothness | Coefficient of Friction |
|---|---|---|---|
| Example 5 | + | 3 | 0.221 |
| Example 6 | + | 3 | 0.193 |
| Example 7 | − | 1 | 0.268 |
| Example 8 | − | 1 | 0.406 |

It can be seen that the comparative examples were distinguishable. In the case of Example 6, the mere physical blend demonstrated poor hydrophobicity and smoothness characteristics, i.e., no enhanced textural behavior, despite I lower coefficient of friction. Comparative Example 7 also lacked any enhanced performance attributes.

TABLE 3

Water absorption

| | Examples | | | | | | | |
|---|---|---|---|---|---|---|---|---|
| | 1 | 2 | 3 | 4 | 5 | 6 | 7 | 8 |
| Water (Grams of water per 100 grams of powder) | 0 | 0 | 0 | 0 | 0 | 0 | 200 | 215 |

In conclusion, it was desirable to have a powder with little to no water absorption. The process achieved a unique product with very low coefficient of friction and no water absorption compared to a physical blend.

Formulations Examples

Formulations with Natural Compositions

Presently, there is an increased demand in the cosmetic and personal care global market for formulations that are sustainable, 100% biobased and biodegradable. The following application examples fulfill this demand, where compositions of examples 8 through 16 were 100% naturally derived.

Example 8—Face Serum

Evaluation on cosmetic application of soft-focus or line blurring effects. Post-addition to serum formulations showcases the ease of addition and texture enhancement. The soft-focus effect can be dependent on the choice of oil used. A volatile and non-volatile oils were evaluated in the same type of application.

Face serums comprising of the powder composite from Example 2 and following composition in Table 2 was prepared according to the following:

TABLE 3

| Phase | INCI Name | Example 8A % w/w | Example 8B % w/w | Example 8C % w/w | Example 8D % w/w |
|---|---|---|---|---|---|
| A | Water | 56.70 | 60.70 | 56.70 | 60.70 |
|  | Xanthan Gum | 0.30 | 0.30 | 0.30 | 0.30 |
|  | Glycerin | 5.00 | 5.00 | 5.00 | 5.00 |
|  | Butylene Glycol | 1.50 | 1.50 | 1.50 | 1.50 |
|  | Glyceryl Caprylate (and) Glyceryl Undecylenate | 1.50 | 1.50 | 1.50 | 1.50 |
| B | Sucrose Polystearate (and) Cetyl Palmitate | 4.00 | 4.00 | 4.00 | 4.00 |
|  | Caprylic/Capric Triglyceride | — | — | 24.00 | 24.00 |
|  | Coconut Alkanes & Coco-Caprylate/Caprate | 24.00 | 24.00 | — | — |
|  | Tocopherol | 1.00 | 1.00 | 1.00 | 1.00 |
|  | Cetyl Alcohol | 1.50 | 1.50 | 1.50 | 1.50 |
|  | Sodium Stearoyl Glutamate | 0.50 | 0.50 | 0.50 | 0.50 |
| C | Example 2 Powder | 4.00 | — | 4.00 | — |
|  | Gloss Units(GU) | 11.0 | 80.2 | 26.0 | 47.9 |

Table 3—Formulation for a volatile emulsion with Example 2 powder (Example 8A), volatile emulsion without powder (Example 8B), Non-volatile emulsion with Example 2 powder (Example 8C), and non-volatile emulsion without powder (Example 8D). Gloss units (GU) measured by a gloss meter.

The ingredients listed in Phase A were combined, heated to 60-65 deg C. and using a Greerco homogenizer, mixed until homogeneous. The ingredients listed in Phase B were combined in a separate vessel, heated to 60-65 deg C. and mixed until homogeneous. While Phase A was mixing add Phase B and mix until emulsion was homogeneous. Switch equipment to an anchor blade type mixer. Add Phase C to Phase AB and mix until homogeneous.

The high gloss unit value in the Volatile Emulsion without powder demonstrates a film with high shine. The value from the gloss meter of Volatile Emulsion with powder demonstrates a film with reduced shine or enhanced mattifying effect. This result indicates that the powder in a volatile emulsion was well suited for use as a soft-focus particle. The high gloss unit value in the Non-volatile emulsion without powder demonstrates a film with high shine. The value from the gloss meter of the Non-volatile emulsion with powder demonstrates a film with reduced shine or enhanced mattifying effect. This result indicates that the powder of Non-volatile emulsion with powder was well suited for use as a soft-focus particle in this type of system as well.

Example 9—Face Cream

A Face cream comprising of the powder composite from Example 2 and following composition in Table 4 was prepared according to the following:

TABLE 4

| Phase | INCI Name | % w/w |
|---|---|---|
| A | Water | 54.50 |
|  | Xanthan Gum | 0.25 |
|  | Glycerin | 4.00 |
|  | Butylene Glycol | 2.00 |
|  | Propanediol & Pentylene Glycol & Phenethyl Alcohol | 2.00 |
|  | Mica & Titanium Dioxide (CI 77891) | 2.00 |

TABLE 4-continued

| Phase | INCI Name | % w/w |
|---|---|---|
| B | Sucrose Polystearate & Cetyl Palmitate | 4.50 |
|  | Coco Caprylate/Caprate | 5.00 |
|  | Tocopherol | 1.00 |
|  | Glyceryl Citrate/Lactate/Linoleate/Oleate | 2.00 |
|  | Octyldodecanol | 4.00 |
|  | Cetearyl Alcohol | 4.50 |
|  | Butyrospermum Parkii Butter | 5.75 |
|  | Dicaprylyl Carbonate | 2.00 |
|  | Triheptanoin | 5.00 |
| C | Example 2 Powder | 1.5.00 |

The ingredients listed in Phase A were combined, heated to 70-75 deg C. and using a Greerco homogenizer, mixed until homogeneous. The ingredients listed in Phase B were combined in a separate vessel, heated to 70-75 deg C. and mixed until homogeneous. While Phase A was mixing add Phase B and mix until emulsion was homogeneous. Switch equipment to an anchor blade type mixer and cool to room temperature while mixing.

Example 10—Natural Sunscreen Lotion with SPF30

A sunscreen lotion with SPF30 comprising of the powder composite from Example 2 and following composition in Table 5 was prepared according to the following:

TABLE 5

| Phase | INCI name | % w/w |
|---|---|---|
| A | Zinc Oxide & Caprylic/Capric Triglyceride & Polyhydroxystearic Acid | 22.0 |
|  | Coco-Caprylate/Caprate & Triheptanoin & C9-12 Alkane & Polyurethane-100 | 5.0 |
|  | Polyglyceryl-6 Polyricinoleate & Polyglyceryl-10 Dioleate | 4.0 |
|  | Coco-Caprylate/Caprate | 7.0 |
|  | Caprylic/Capric Triglyceride | 15.5 |
|  | Polyhydroxystearic Acid | 0.7 |
|  | Olive Squalane | 5.0 |
|  | Tocopherol | 1.0 |
|  | Polyglyceryl-2 Dipolyhydroxystearate | 2.0 |

TABLE 5-continued

| Phase | INCI name | % w/w |
|---|---|---|
| | Octyldodecanol & Octyldodecyl Xyloside | 2.0 |
| | Example 2 Powder | 3.0 |
| B | Water | 25.8 |
| | Hectorite | 0.5 |
| | Propanediol | 4.0 |
| | Sodium Chloride | 1.0 |
| | Glyceryl Caprylate (and) Glyceryl Undecylenate | 1.5 |

The ingredients listed in Phase A were combined using a Greerco homogenizer, mixed until homogeneous. From Phase B, Hectorite was mixed with propanediol to prepare the slurry. The ingredients listed in Phase B were combined in a separate vessel and mixed until homogeneous. The slurry of Hectorite and propanediol was added to Phase B. While Phase A is mixing add Phase B and mix until emulsion is homogeneous. Switch equipment to an anchor blade type mixer and cool down to room temperature.

Example 11—Mousse Foundation

A mousse foundation comprising of the powder composite from Example 2 and following composition in Table 6 was prepared according to the following:

The ingredients listed in Phase A were combined using a Greerco homogenizer, mixed until homogeneous. The ingredients listed in Phase B were combined in a separate vessel and micro pulverized until the color was homogeneous. From Phase C, Hectorite was mixed with Glycerin to prepare the slurry. The ingredients listed in Phase C were combined in a separate vessel using a 3-prong propeller and mixed until homogeneous. The slurry of Hectorite and Glycerin were added to Phase C. The ingredients listed in Phase D were mixed in the separate vessel and added to Phase C. While Phase AB was mixing add Phase CD and mix until emulsion was homogeneous. The equipment was switched to an anchor blade type mixer and Phase E was added to the vessel. For formulation listed in example 11B, 11C and 11D Phase F was added with an anchor blade type mixer. Viscosity was evaluated using a Brookfield DMI+ viscometer at 25 C, with spindle T-F and velocity 0.6 RPM.

In the mousse foundation, the emulsifying system may also comprise different glyceryl fatty acid esters, such but not limited to as Polyglyceryl-10 Laurate, Polyglyceryl-3 Diisostearate, Polyglyceryl-6 Distearate, Polyglyceryl-10 Dipalmitate, Polyglyceryl-3 Behenate.

As seen in Table 6, as the percentage of powder increases the viscosity also increases, resulting in a more stable formulation. As viscosity of the formulation increased, there was an equivalent gradual enhancement of matte appear-

TABLE 6

| Phase | INCI Name | Example 11A % w/w | Example 11B % w/w | Example 11C % w/w | Example 11D % w/w |
|---|---|---|---|---|---|
| A | Coco-Caprylate/Caprate | 16 | 10 | 10 | 10 |
| | Coco-Caprylate/Caprate & Triheptanoin & C9-12 Alkane & Polyurethane-100 | 15 | 15 | 15 | 15 |
| | Polyglyceryl-6 Polyricinoleate & Polyglyceryl-10 Dioleate | 8 | 8 | 8 | 8 |
| | Lecithin | 1.5 | 1.5 | 1.5 | 1.5 |
| | Tocopherol | 1.2 | 1.2 | 1.2 | 1.2 |
| | Coconut Alkanes & Coco-Caprylate/Caprate | 1 | 1 | 1 | 1 |
| B | Titanium Dioxide & Disodium Stearoyl Glutamate & Aluminum Hydroxide | 7.2 | 7.2 | 7.2 | 7.2 |
| | Iron Oxides (CI 77492) & Disodium Stearoyl Glutamate & Aluminum Hydroxide | 2.1 | 2.1 | 2.1 | 2.1 |
| | Iron Oxides (CI 77491) & Disodium Stearoyl Glutamate & Aluminum Hydroxide | 0.47 | 0.47 | 0.47 | 0.47 |
| | Iron Oxides (CI 77499) & Disodium Stearoyl Glutamate & Aluminum Hydroxide | 0.19 | 0.19 | 0.19 | 0.19 |
| C | Water | 29.37 | 33.37 | 29.37 | 25.37 |
| | Hectorite | 2.00 | 2.00 | 2.00 | 2.00 |
| | Glycerin | 5.00 | 5.00 | 5.00 | 5.00 |
| | Butylene Glycol | 3.00 | 3.00 | 3.00 | 3.00 |
| | Glyceryl Caprylate (and) Glyceryl Undecylenate | 1.50 | 1.50 | 1.50 | 1.50 |
| | Acacia Senegal Gum & Xanthan Gum | 0.07 | 0.07 | 0.07 | 0.07 |
| D | Water | 5.00 | 5.00 | 5.00 | 5.00 |
| | Sodium Chloride | 0.70 | 0.70 | 0.70 | 0.70 |
| E | Silica | 0.70 | 0.70 | 0.70 | 0.70 |
| F | Example 2 Powder | — | 2.00 | 6.00 | 10.00 |
| | Viscosity (cPs) | 198,750 | 458,500 | 502,750 | 729,750 | ance, coverage as well as color strength. Moreover, there was an observable increase in long wear with better transfer-resistance as well as a texture improvement, seen as a slip, soft and powdery after feel.

Figure 1:
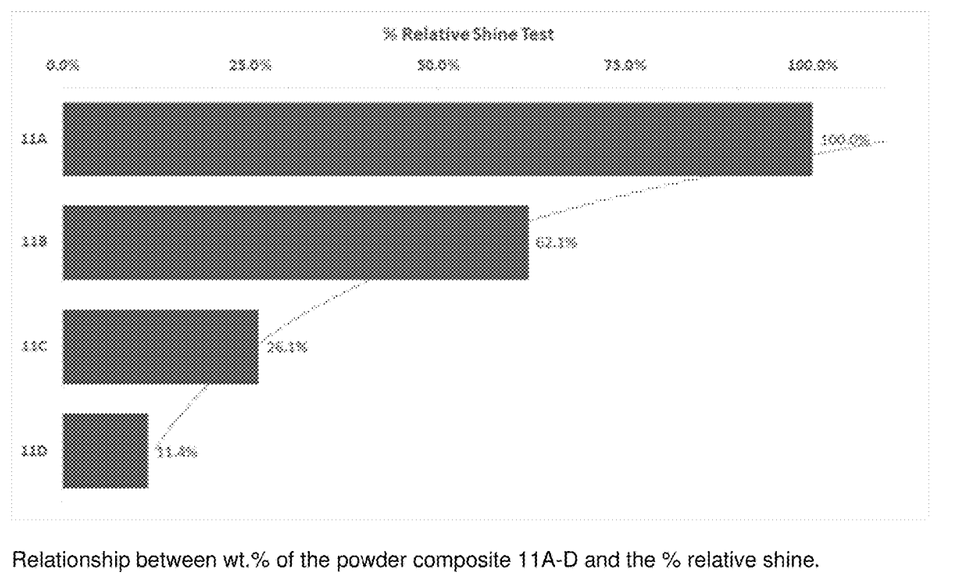
FIG. 1 illustrates the relationship between wt. % of the powder composite in formulations 11-A-D of Example 11 and the % relative shine as measured by a glossmeter.

Using the gloss meter, each application was evaluated for % Relative Shine. As the wt. % of the powder composite from Example 2 increases, there was a decrease in Relative Shine. The results were shown in FIG. 1.

Example 12—Eyeshadow

An eyeshadow comprising of the powder composite from Example 1 and following composition in Table 7 was prepared according to the following:

TABLE 7

| Phase | INCI Name | % w/w |
|---|---|---|
| A | Water | 57.70 |
|  | Caesalpinia Spinosa Gum | 0.30 |
|  | Glycerin | 5.00 |
|  | Glyceryl Caprylate (and) Glyceryl Undecylenate | 1.50 |
| B | Coco-Caprylate/Caprate | 2.00 |
|  | Triheptanoin | 2.00 |
|  | Palmitic Acid | 1.00 |
|  | Stearic Acid | 1.50 |
|  | Tocopherol | 1.00 |
|  | Glyceryl Stearate SE | 1.50 |
|  | Coco-Caprylate/Caprate & Triheptanoin & C9-12 Alkane & Polyurethane-100 | 5.00 |
|  | Lauryl Glucoside | 1.80 |
|  | Example 2 Powder | 3.00 |
| C | Mica | 3.70 |
|  | Iron Oxide (CI 77491) & Mica | 9.00 |
|  | Mica & Titanium Dioxide (CI 77891) & Iron Oxide (CI 77491) | 4.00 |

The ingredients listed in Phase A were combined, heated to 70-75 deg C. and using a Greerco homogenizer, mixed until homogeneous. The ingredients listed in Phase B were combined in a separate vessel, heated to 70-75 deg C. and mixed until homogeneous. While Phase A was mixing add Phase B and mix until emulsion was homogeneous. The ingredients listed in Phase C were added sequentially to the Phase AB. Switch equipment to an anchor blade type mixer and cool to room temperature while mixing.

The eyeshadow formulation composition base in Table 6 was also used to make a highlighter, by simply substituting pigments in Phase C, but other mineral derived pigments. These were Gemtone Tan Opal (BASF) and Timiron Super Silver (EMD Performance Materials) and quantum satis with water. Table 6 composition was another example of formulation with increased long wear and transfer-resistance even in the absence of resin polymer.

Example 13—Primer

A primer comprising of the powder composite from Example 2 and following composition in Table 8 was prepared according to the following:

TABLE 8

| Phase | INCI name | % w/w |
|---|---|---|
| A | Coco-Caprylate/Caprate & Triheptanoin & C9-12 Alkane & Polyurethane-100 | 50.10 |
|  | Coconut Alkanes & Coco-Caprylate/Caprate | 6.00 |
|  | Octyldodecyl PCA | 25.50 |
|  | Hydrated Silica | 10.00 |

TABLE 8-continued

| Phase | INCI name | % w/w |
|---|---|---|
|  | Silica | 1.50 |
|  | Example 2 Powder | 2.00 |

The ingredients listed in Phase A were combined using a 3-prong mixer, mixed until homogeneous.

The formulation in Table 7 is an example that mimics silicone's superb feel. Silicones in the elastomeric or powder form exhibit silky, smooth with cushion and powdery after feel on the skin. The primer shows the same characteristics on skin application while being 100% naturally derived.

Example 14—Eyeliner

An eyeliner comprising of the powder composite from Example 2 and following composition in Table 9 were prepared according to the following:

TABLE 9

| Phase | INCI name | % w/w |
|---|---|---|
| A | Water | 50.10 |
|  | Caesalpinia Spinosa Gum | 0.30 |
|  | Glycerin | 5.00 |
|  | Phenethyl Alcohol & Pentylene Glycol & Propanediol | 2.00 |
|  | Iron Oxide (CI 77499) | 15.00 |
| B | Palmitic Acid | 1.00 |
|  | Stearic Acid | 3.00 |
|  | Tocopherol | 1.00 |
|  | Glyceryl Stearate SE | 3.00 |
| C | Coco-Caprylate/Caprate & Triheptanoin & C9-12 Alkane & Polyurethane-100 | 10.00 |
|  | Lauryl Glucoside | 2.00 |
|  | Example 2 Powder | 3.00 |
|  | Zea Mays (Corn) Starch | 4.60 |

The ingredients listed in Phase A were combined, heated to 70-75 deg C. and using a Greerco homogenizer, mixed until homogeneous. The ingredients listed in Phase B were combined in a separate vessel, heated to 70-75 deg C. and mixed until homogeneous. While Phase A is mixing add Phase B and mix until emulsion was homogeneous. The ingredients listed in Phase C were added sequentially to the Phase AB. Switch equipment to an anchor blade type mixer and cool to room temperature while mixing.

The eyeliner formulation composition base in Table 9 was also used to make a mascara, where Iron Oxide (CI 77499) was replaced with carbon black at an appropriate percentage to achieve mascara requirements. Here we were seeing better composite powder in systems utilizing different types of naturally occurring minerals, such as but not limited to carbon black. This formula with time, also showed an improved long wear and transfer-resistance.

Example 15—Lipstick

A lipstick comprising of the powder composite from Example 2 and following composition in Table 10 was prepared according to the following:

TABLE 10

| Phase | INCI Name | % w/w |
|---|---|---|
| A | Euphorbia Cerifera (Candelilla) Wax | 13.00 |
|  | Copernica Cerifera (Carnauba) Wax | 3.00 |

TABLE 10-continued

| Phase | INCI Name | % w/w |
|---|---|---|
| | Beeswax | 2.00 |
| | Prunus Amygdalus Dulcis (Sweet Almond) Oil | 13.00 |
| | Polyhydroxystearic Acid | 3.00 |
| | Octyldodecanol | 5.00 |
| | Cocos Nucifera (Coconut) Oil | 1.50 |
| | Example 2 Powder | 5.00 |
| | Coco-Caprylate/Caprate & Triheptanoin & C9-12 Alkane & Polyurethane-100 | 15.00 |
| | Ricinus Communis Seed Oil & Red 7 | 30.00 |
| | Titanium Dioxide (and) Castor Oil | 8.00 |
| | Silica | 0.40 |
| | Sucralose | 0.10 |
| | Tocopherol | 1.00 s |

The ingredients listed in Phase A were combined, heated to 90-95 C using a 3-prong mixer, mixed until homogeneous. The samples were poured into a lipstick component at 70-75 C.

Addition of the novel composite powder from Example 2 to lipstick formulation in Table 9 shows better compatibility in these types of anhydrous systems, which included naturally derived waxes, such as beeswax, candelilla and carnauba waxes as well as with naturally derived vegetable oils, such as sweet almond and coconut oil. Ease of incorporation of the powder in the formula due to its better suspension capability consequently contributing to a sweat-free, more stable formulation stability. On lip application, a more matte and cushion was seen.

Formulations with Synthetic and Natural Compositions

Example 16—Water in Oil Sunscreen Fluid SPF 26

Table 11—Formulation of a water in oil sunscreen without Example 2 powder (Example 16A), and water in oil sunscreen with Example 2 powder (Example 16B). SPF in-vitro measured by Labsphere 2000.

The ingredients listed in Phase B were combined, heated to 80-85 C using a Greerco homogenizer, mixed until homogeneous. The ingredients listed in Phase A were combined, heated to 70-75 C using propeller in a separate vessel and mixed until homogeneous. While Phase B was mixing add Phase A and mix until emulsion was homogeneous. While Phase AB was mixing add Phase C and mix until homogeneous. The equipment was switched to a side sweep type mixer and cooled down to room temperature.

SPF value of a sunscreen greatly depends on how the sunscreen actives, whether mineral or organic, interact with other ingredients as well as how these ingredients were able to contribute to blocking UVA and UVB in the formula. Addition of Example 2 powder to a water in oil sunscreen containing Zinc Oxide, provided a boost in SPF with 2 units increase.

Example 17—Water in Silicone Sunscreen Cream SPF 30

A sunscreen cream with SPF 30 comprising of the powder composite from Example 2 and following composition in Table 12 were prepared according to the following:

TABLE 11

| Phase | INCI Name | Example 16A % w/w | Example 16B % w/w |
|---|---|---|---|
| A | Water | 12.00 | 12.00 |
| | Zemea | 7.00 | 7.00 |
| | Benzyl Alcohol & Salicylic Acid & Glycerin & Sorbic Acid | 1.00 | 1.00 |
| | Water & Boswellia Serrata Extract & Centella Asiatica Extract & Betula Alba Bark Extract & Polygonum Cuspidatum Root Extract & Phenoxyethanol & Sodium Benzoate | 3.00 | 3.00 |
| | Simethicone | 0.10 | 0.10 |
| | Tromethamine | 0.30 | 0.30 |
| | Polysorbate 20 | 0.10 | 0.10 |
| B | C12-15 Alkyl Benzoate | 4.50 | 3.50 |
| | Coco-Caprylate/Caprate | 3.00 | 3.00 |
| | Ethylhexyl Palmitate | 3.00 | 3.00 |
| | Polyglyceryl-6 Polyricinoleate & Polyglyceryl-10 Dioleate | 8.00 | 8.00 |
| | Zinc Oxide & Caprylic/Capric Triglyceride & Polyhydroxystearic Acid | 25.00 | 25.00 |
| | Lecithin | 1.00 | 1.00 |
| | Isododecane & Disteardimonium Hectorite & Propylene Carbonate | 7.00 | 7.00 |
| | Example Sample 2 | — | 1.00 |
| C | Dimethicone & Polysilicone-11 & Butyrospermum Parkii (Shea) Butter & Water & Glycerin & Decyl Glucoside | 10.00 | 10.00 |
| | Isododecane & Polymethylsilsesquioxane/Trimethylsiloxysilicate | 10.00 | 10.00 |
| | Polymethylsilsesquioxane | 3.00 | 3.00 |
| | Aluminum Starch Octenylsuccinate | 2.00 | 2.00 |
| | In-vitro SPF | 26 | 28 |

TABLE 12

| Phase | INCI Name | Example 17A % w/w | Example 17B % w/w |
|---|---|---|---|
| A | Titanium Dioxide & Dimethicone & Hexyl Laurate & Stearic Acid & PEG-10 Dimethicone & Polyhydroxystearic Acid | 10.00 | 10.00 |
|  | Zinc Oxide & Cyclopentasiloxane & PEG-10 Dimethicone | 15.00 | 15.00 |
|  | Olive Squalane | 2.00 | 2.00 |
|  | Cetyl PEG/PPG-10/1 Dimethicone | 3.00 | 3.00 |
|  | Dimethicone & PEG/PPG-18/18 Dimethicone | 3.00 | 3.00 |
|  | Tocopheryl Acetate | 0.10 | 0.10 |
|  | Polymethylsilsesquioxane | 3.00 | 3.00 |
|  | Isododecane & Polymethylsilsesquioxane & PEG-10 Dimethicone | 10.00 | 10.00 |
|  | Isododecane & Disteardimonium Hectorite & Propylene Carbonate | 18.25 | 17.25 |
|  | Example 2 Powder | — | 1.00 |
| B | Water | 29.85 | 29.85 |
|  | Butylene Glycol | 4.00 | 4.00 |
|  | Phenoxyethanol & Caprylyl Glycol & Potassium Sorbate & Water & Hexylene Glycol | 1.00 | 1.00 |
|  | Polysorbate 20 | 0.50 | 0.50 |
|  | Panthenol | 0.10 | 0.10 |
|  | Decyl Glucoside | 0.20 | 0.20 |
|  | In-vitro SPF | 30 | 34 |

Table 12—Formulation of a water in silicone sunscreen without Example 2 powder (Example 17A), and water in silicone sunscreen with Example 2 powder (Example 17B). SPF in-vitro measured by Labsphere 2000.

The ingredients listed in Phase A were combined using a Greerco homogenizer, mixed until homogeneous. The ingredients listed in Phase B were combined using a 3-prong propeller in a separate vessel and mixed until homogeneous. While Phase A was mixing add Phase B and mix until emulsion was homogeneous.

Addition of Example 2 powder to a water in silicone sunscreen containing Titanium and Zinc Oxide, provided a boost in SPF with 4 units increase.

Example 18—Body Powder

The powder composite from Example 3 was used for body powder composition. 50 parts of Example 3 and 50 parts for cornstarch were mixed using a tumbler and 0.1 part of fragrance was added to the body powder composition and tumbled. Upon evaluation the composition from Example 16 had enhanced spreadability and smoothness compared to 100 parts cornstarch.

We claim:

1. A powder composition, comprising a hydrophobic, fused powder composite being a heated, reacted blend of
   a. a ferment in an amount from about 70% to about 95% by weight of the composition, wherein the ferment is isolated from yeast origin, and the yeast is Saccharomyces; and
   b. an amino acid derivative in an amount from about 5% to about 30% by weight of the composition, wherein the amino acid derivative is a lysine derivative; and
   wherein the ferment and the amino acid derivative have been micronized until a temperature of at least 105° C. is reached and the resultant micronized powder is held at that temperature for a time period of at least 15 minutes to provide the powder composition with Coefficient of Friction of from 0.1 to 0.25.

2. The powder composition of claim 1, wherein the amount of ferment is from about 80 to about 95% by weight and the amount of the amino acid derivative is from about 5% to about 20% by weight.

3. The powder composition of claim 1, wherein the heated, reacted blend of ferment and amino acid derivative have been micronized until a temperature of from about 107° C. to about 165° C. is reached and the resultant micronized powder is held at that temperature for a time period of at least one hour.

4. The powder composition of claim 3, wherein the time period is from about 1 to about 3 hours.

5. The powder composition of claim 1, wherein the powder composition was substantially hydrophobic and has zero water absorption by spatula rub-out method (ASTM D281).

6. The powder composition of claim 1, wherein the powder composition is a free-flowing powder and has a bulk density from 0.15 g/ml to 0.25 g/mL.

7. The powder composition of claim 1, wherein the particle size distribution of the hydrophobic, fused powder composite containing the ferment and the amino acid derivative particles is from about 0.1 microns to about 120 microns.

8. The powder composition of claim 7, wherein the particle size distribution of the hydrophobic, fused powder composite containing the ferment and the amino acid derivative particles is from about 0.1 microns to about 50 microns.

9. The powder composition of claim 1, wherein the lysine derivative is an N-acylated lysine.

10. The powder composition of claim 9, wherein the N-acylated lysine is N6-lauroyl -L-lysine.

11. The powder composition of claim 1, wherein the ferment comprises a polyhydroxyalkanoate.

12. The powder composition of claim 11, wherein the polyhydroxyalkanoate is a polyhydroxybutyrate or a derivative thereof.

13. The powder composition of claim 11, wherein the polyhydroxyalkanoate is selected from the group consisting of polyhydroxybutyrate (PHB), polyhydroxyvalerate (PHV), polyhydroxybutyratevalerate (PHBV), polyhydroxyhexanoate (PHH), and combinations thereof.

14. The powder composition of claim 1, further comprising an ancillary ingredient.

15. A soft-focus cosmetic composition comprising at least 1% wt. of the powder composition of claim 1.

16. The soft-focus cosmetic composition of claim 15, wherein the powder composition comprises from about 1 to about 30% wt. of the soft-focus composition.

17. A body powder composition comprising from about 50 to about 99% by weight of the powder composition of claim 1, and from about 1 to 50% by weight cornstarch.

18. The body powder composition of claim 17, wherein the powder composition is present in an amount of from about 70 to about 99% by weight and the amount of corn starch is from about 1 to about 30% by weight cornstarch.

19. A topical cosmetic composition comprising from about 0.1% to about 50% by weight of the powder composition of claim 1.

20. A cosmetic ingredient consisting essentially of the powder composition of claim 1.

21. The powder composition of claim 20, wherein the ferment includes a polyhydroxyalkanoate and the amino acid derivative is an N-acylated amino acid derivative.

22. A powder composition, comprising a hydrophobic, fused powder composite being a heated, reacted blend of
 a. a ferment in an amount from about 70% to about 95% by weight of the composition, wherein the ferment is isolated from yeast origin, and the yeast is Saccharomyces; and
 b. an amino acid derivative in an amount from about 5% to about 30% by weight of the composition, wherein the ferment is polyhydroxyalkanoate and the amino acid derivative is an N-acylated lysine, and
 wherein the ferment and the amino acid derivative have been micronized until a temperature of at least 105° C. is reached and the resultant micronized powder is held at that temperature for a time period of at least 15 minutes to provide the powder composition with Coefficient of Friction of from 0.1 to 0.25.

23. The powder composition of claim 22, wherein the polyhydroxyalkanoate is a polyhydroxybutyrate or a derivative thereof and the N-acylated lysine is N6-lauroyl-L-lysine.

24. The powder composition of claim 1, wherein the ferment is polyhydroxyalkanoate, and the amount of the polyhydroxyalkanoate is from about 80% to about 95% by weight and the amount of amino acid derivative is from about 5% to about 20% by weight.

25. The powder composition of claim 22, wherein the amount of the polyhydroxyalkanoate is from about 80% to about 95% by weight and the amount of amino acid derivative is from about 5% to about 20% by weight.

26. The powder composition of claim 1, wherein the hydrophobic, fused powder composite has a coefficient of friction of 0.232 or less.

* * * * *

UNITED STATES PATENT AND TRADEMARK OFFICE
CERTIFICATE OF CORRECTION

| | | |
|---|---|---|
| PATENT NO. | : 12,337,059 B2 | Page 1 of 1 |
| APPLICATION NO. | : 17/479122 | |
| DATED | : June 24, 2025 | |
| INVENTOR(S) | : Ronald V. Lerum et al. | |

It is certified that error appears in the above-identified patent and that said Letters Patent is hereby corrected as shown below:

In the Claims

In Claim 5:
Column 22, Line 2 "was" should read --is--.

In Claim 16:
Column 23, Line 2 "powder" should read --soft-focus--.
Column 23, Line 3 "soft-focus" should read --powder--.

In Claim 21:
Column 23, Line 1 "powder" should read --cosmetic--.

Signed and Sealed this
Twenty-first Day of October, 2025

John A. Squires
*Director of the United States Patent and Trademark Office*